United States Patent [19]
Roche

[11] Patent Number: 4,865,609
[45] Date of Patent: Sep. 12, 1989

[54] MODULAR JOINT PROSTHESIS ASSEMBLY AND METHOD OF REMOVING

[75] Inventor: Karen M. Roche, Stillwater, Minn.

[73] Assignee: Bioconcepts, Inc., Stillwater, Minn.

[21] Appl. No.: 163,054

[22] Filed: Mar. 2, 1988

[51] Int. Cl.[4] .................... A61F 2/36; A61F 5/04
[52] U.S. Cl. ......................... 623/23; 623/18;
128/92 VT; 128/303 R; 433/161; 254/100
[58] Field of Search ............... 623/22, 23, 18, 19,
623/20, 21; 128/92 R, 92 V, 92 VY, 92 VZ, 92
VV, 92 VW, 92 VT, 303 R; 433/161, 174;
254/100

[56] References Cited

U.S. PATENT DOCUMENTS

| | | | |
|---|---|---|---|
| 1,109,096 | 9/1914 | West | 433/161 X |
| 2,821,776 | 2/1958 | Keister | 254/100 |
| 3,067,740 | 12/1962 | Haboush . | |
| 3,102,536 | 9/1963 | Rose et al. | 623/23 |
| 3,815,157 | 6/1974 | Skorecki et al. . | |
| 3,818,512 | 6/1974 | Shersher . | |
| 3,863,273 | 2/1975 | Averill . | |
| 3,869,730 | 3/1975 | Skobel . | |
| 3,889,299 | 6/1975 | Osborne et al. . | |
| 3,889,376 | 6/1975 | Zatkin | 433/161 |
| 3,906,550 | 9/1975 | Rostoker et al. | 623/18 X |
| 3,965,490 | 6/1976 | Murray et al. . | |
| 3,984,297 | 7/1975 | Mittelmeier et al. . | |
| 3,987,499 | 10/1976 | Scherbach et al. . | |
| 3,996,625 | 12/1976 | Noiles . | |
| 4,030,143 | 6/1977 | Elloy et al. . | |
| 4,040,131 | 8/1977 | Gristina . | |
| 4,051,559 | 10/1977 | Pifferi | 623/22 |
| 4,059,883 | 11/1977 | Osborne . | |
| 4,100,626 | 7/1978 | White | 128/92 V X |
| 4,199,824 | 4/1980 | Niederer . | |
| 4,206,517 | 6/1980 | Pappas et al. . | |
| 4,261,062 | 4/1981 | Amstutz et al. . | |
| 4,406,023 | 9/1983 | Harris . | |
| 4,408,360 | 10/1983 | Keller . | |
| 4,435,854 | 3/1984 | Keller . | |
| 4,502,197 | 3/1985 | Harder . | |
| 4,520,511 | 6/1985 | Gianezio et al. . | |
| 4,528,702 | 7/1985 | Frey . | |
| 4,586,932 | 5/1986 | Scales . | |
| 4,676,797 | 6/1987 | Anapliotis et al. . | |
| 4,676,798 | 6/1987 | Noiles . | |
| 4,686,971 | 8/1987 | Harris et al. | 128/92 VT |

FOREIGN PATENT DOCUMENTS 1371335 10/1974 United Kingdom ............... 623/23

OTHER PUBLICATIONS

Biomet, Inc., "Bio-Modular Total Shoulder", undated advertising (Warsaw, Indiana 46580), and Form No. Y-BMT-087/013188.

Zimmer, Inc., "Fenlin Total Shoulder, an Exclusive, Modular Design Encourages Surgical Latitude and Ease of Insertion", 1988.

Zimmer, Inc., "Fenlin Total Shoulder Surgical Technique for Total Shoulder Replacement", by John M. Fenlin, Jr., M.D., 1988.

Primary Examiner—Richard J. Apley
Assistant Examiner—David J. Bender
Attorney, Agent, or Firm—Kinney & Lange

[57] ABSTRACT

An improved modular prosthetic joint has a stem portion embedded in a bone with a removable bearing head frictionally mounted on the stem portion. The bearing head has a bore which mates with a tapered shaft of the stem portion. The bearing head has a generally thin wall defining its continuous and unbroken bearing outer surface, with a wall portion extending directly over the tapered shaft which is thinner than the remainder of the bearing head wall. A puller engages an annular shoulder of the bearing head to pierce through the thinner wall portion of the bearing head, engage the tapered shaft and urge the bearing head away from the tapered shaft. Thus, the bearing head is pierced and removed from its associated stem portion, and second replacement bearing head is then mountable on the tapered shaft by impaction.

11 Claims, 2 Drawing Sheets

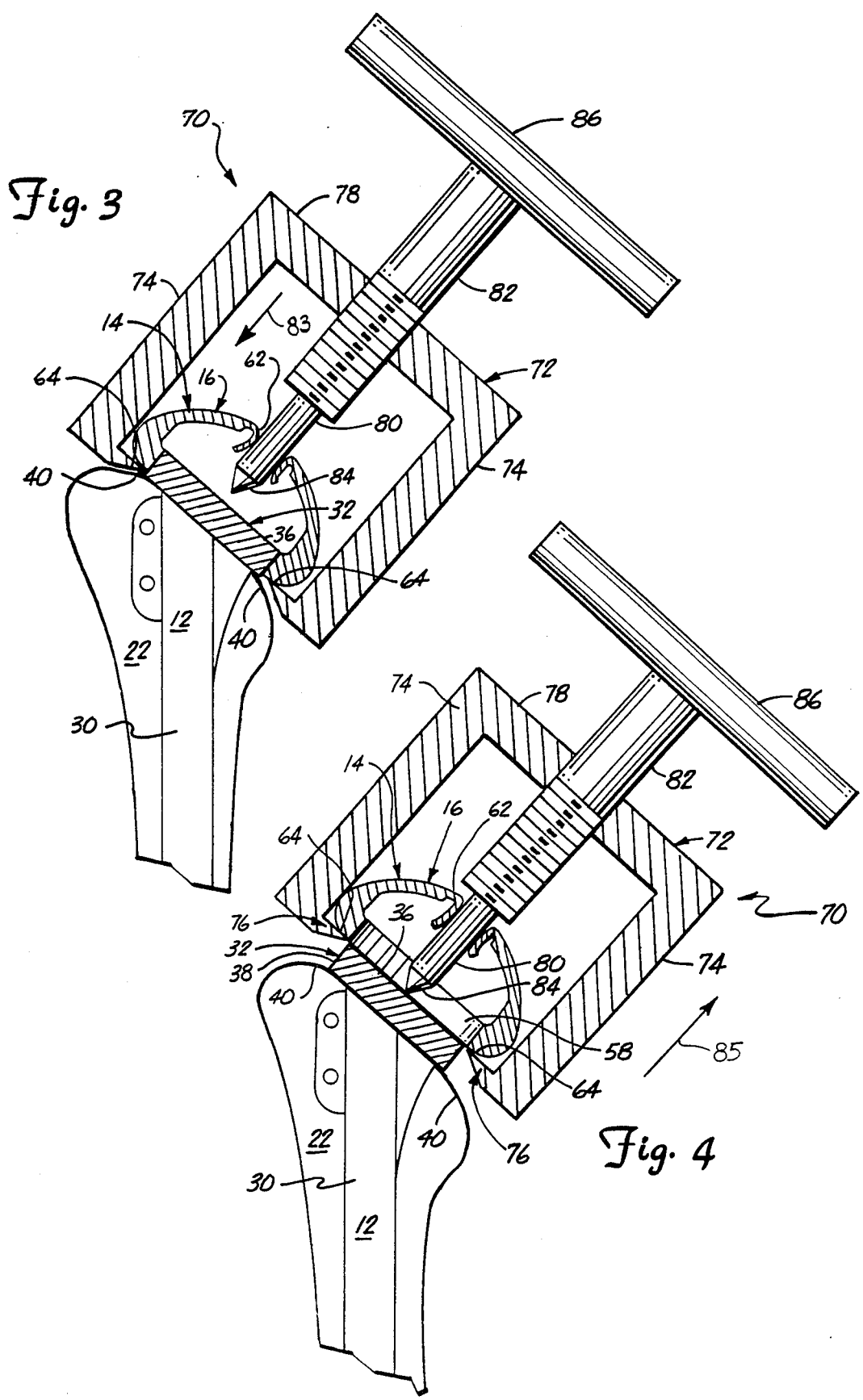

MODULAR JOINT PROSTHESIS ASSEMBLY AND METHOD OF REMOVING

BACKGROUND OF THE INVENTION

1. Field of the Invention.

This invention relates generally to joint prostheses, and more particularly to a modular bearing component for an artificial joint and method of replacement thereof.

2. Description of the Prior Art.

Numerous artificial joint devices have been developed. In such joints as the shoulder or hip, the artificial or prosthetic joint typically includes a bearing head and bearing socket which are pivotable or rotatable with respect to one another, and each connected to opposing bone structures. From time to time, deterioration, infection or patient growth will necessitate a change in the prosthetic joint structure, such as providing a different sized bearing head or replacing one or more components of the prosthetic joint. For this reason, modular prosthesis systems have also been developed.

Modular prosthesis systems are broadly accepted in the field of total hip replacements, with virtually all major orthopedic manufacturers in the United States and abroad offering femoral stem components with interchangeable bearings secured to the stem component by a self-locking tapered arrangement ("Morse" taper). The basic design for such hip prosthesis systems is essentially identical, and consists of a male shank which is machined on the femoral stem and which has a diameter in the range of 0.500 inches, a length of approximately 0.400 to 0.700 inches, and an approximately three degree included angle taper on the diameter. Bearing components of different diameters are machined with an identical matching female taper and are assembled with the femoral stem by impaction. One example of such an arrangement is shown in Harris U.S. Pat. No. 4,406,023.

Once a bearing component has been impacted onto a femoral stem, it is firmly secured thereto and requires considerable axial opposing forces to cause disassembly. Such modular prosthesis systems provide a number of advantages, including the requirement of lower femoral stem inventories associated with the use of different diameter bearing components for the same stem, and the adjustability of the effective length of the neck portion of a stem by changing the depth of the female taper of the bearing components. In addition, surgical exposure during revision or replacement surgery is improved by the bearing component being removable, and the bearing components themselves are easily changeable during such surgery.

Essentially all of the modular hip prosthesis systems include a device or specific structural feature to facilitate removal of the bearing component from the femoral stem during such surgery. These devices or features provide a means for applying an axial opposing force to the inferior margin of the bearing component (typically adjacent the female taper thereon) and usually involve a wedge or similar device which is driven between the underside of the bearing component and a broad collar and/or similar surface of the femoral stem.

While the use of modular bearing components connected via the Morse taper is widespread with respect to prosthetic hip systems, it has not yet gained acceptance in artificial shoulder joints. The functional anatomy of the shoulder differs greatly from the hip, due principally to the dramatically greater range of motion required for optimal shoulder function. Thus, while the extension of the modularity concept to a shoulder prosthesis (i.e., a prosthetic stem with interchangeable bearing components) seems advantageous, certain physical obstacles must be overcome.

The following United States patents illustrate various schemes for prosthetic shoulder joints:

| U.S. Pat. No. | Inventor | Issue Date |
| --- | --- | --- |
| 3,815,157 | Skorecki et al. | 6/11/74 |
| 3,869,730 | Skobel | 3/11/75 |
| 4,030,143 | Elloy et al. | 6/21/77 |
| 4,040,131 | Gristina | 8/9/77 |
| 4,206,517 | Pappas et al. | 6/10/80 |

Each of these arrangements presents a somewhat complex joint, which necessarily requires the removal of more adjacent bone structure than desired in order to accommodate the prosthesis joint. Amstutz et al. U.S. Pat. No. 4,261,062 shows a shoulder joint prosthesis which is much simpler in design and requires less bone removal, but does not provide a modular bearing component arrangement.

Perhaps the main reason that modularity has not yet gained acceptance in prosthetic shoulder joint schemes is anatomical. The anatomy of the humerus does not include a lengthened neck extending between the humeral head and shaft. Unlike a femoral component, therefore, there is no "neck" on an anatomically designed humeral stem component. The provision for such a neck requires the removal of more bone from the humerus than desired, and in prior art integral humeral stem prostheses, the inferior margin of the bearing is preferably placed in direct proximity with the level of resection of the humerus. A humeral stem component fabricated with a typical small diameter male tapered shank (i.e., 0.500 inches) to accommodate a bearing component with a mating female taper bore would, when assembled, have an identical appearance to a conventionally integral humeral stem prosthesis. When implanted, however, the inferior margin of such a modular humeral bearing component would transfer forces directly to the resected humerus and not necessarily to the humeral stem component. The absence of compressive force maintained between the bearing and stem components would permit separation of those components and distal migration of the stem component, which of course would result in clinical failure. In addition, the close proximity of the inferior margin of the bearing component and humerus (with no exposed shoulder of the humeral stem component therebetween) means removal of the bearing component from frictional engagement with the humeral stem component requires the exertion of an opposing force directly between the inferior margin of the bearing component and the humerus itself, with the potential for damaging the humerus, an obviously undesirable consequence of using a modular humeral bearing.

Three modular shoulder prosthesis systems are known, the "Fenlin Total Shoulder" by Zimmer, Inc., the "Bio-Modular Total Shoulder" by Biomet, Inc., and a third by Interedics Orthopedics. In the first two systems, a proximal disk-shaped flange is provided on the humeral stem component, with a male Morse taper shaft extending upwardly therefrom. In the Interedics shoulder, the proximal flange is a portion of a disk, which extends anteriorly and posteriorly from the central Morse taper shaft. In all three systems, a solid metal bearing component with a female Morse taper on its marginal side is frictionally mounted onto the male Morse taper shaft. Removal of the bearing component from the humeral stem is accomplished by exerting a prying force between the marginal side of the bearing component and the proximal flange of the humeral stem component. To facilitate such prying, a slight gap is provided between the marginal side of the bearing component and the exposed surface of the flange. In earlier, one-piece humeral bearing implants, efforts have been made to be certain that all exposed margins of the bearing component are as smooth and rounded as possible, not only to effectuate a smooth rotation of the bearing component on the glenoid, but also because the various tendons of the shoulder, particularly the rotator cuff tendons, must ride directly across the surface of the bearing component. In a total shoulder replacement patient, the rotator cuff tendons are often attenuated and weakened, and the discontinuity caused by the gap between the marginal surface of the bearing component and the flat edges of the proximal flange in the "Fenlin," "Bio-Modular," and Intermedics shoulder systems is undesirable, because it may contribute to further weakening of the tendons. In addition, the bearing components for the "Fenlin," "Bio-Modular," and Intermedics shoulder systems are solid metal, and thus relatively heavy, which can be significant in the function of a limb suspended against gravity.

SUMMARY OF THE INVENTION

The present invention provides modular prosthetic joint components which are simple and efficient in design, and which functionally perform (from the patient's point of view) in the same manner as integral joint prostheses, while potentially being lighter in weight. In addition, the present invention provides a method of assembly and disassembly of prosthetic joint components which is not only easy to use, but requires no further resection of the bone or forcing against the bone during the separation process.

The present invention, in both apparatus and method forms, relates particularly to the unique design for a bearing component in a modular prosthetic joint. In such a prosthetic joint, a stem component is provided with a tapered shaft at one end thereof. The unique bearing component of the present invention has a bore therein which frictionally mates with the tapered shaft for mounting the bearing component on the stem component. A portion of the bearing component which extends over the tapered shaft is formed of relatively thin material. An outer surface of the bearing component defines an annular shoulder portion adjacent and about the bore therein. Means are provided for engaging the annular shoulder portion, and further means associated therewith are provided for piercing through the relatively thin material at the apex of the dome of the bearing component to engage the tapered shaft and urge the bearing component away from the tapered shaft. Preferably, the engaging means comprises a puller body which has a plurality of leg portions adapted to engage the annular shoulder portion of the bearing head. The piercing means is movably mounted with respect to the puller body and aligned to move along a longitudinal axis defined by the tapered shaft into engagement with the relatively thin portion of the bearing component, through such material and into engagement with the outer end of the tapered shaft.

In performing the method of the present invention for removing a bearing component from frictional engagement with its tapered shaft, a puller body is first aligned about the bearing component so that a lower portion of the puller body engages a lower shoulder surface of the bearing component in a plane generally normal to a longitudinal axis defined by the tapered shaft. Then, the central upper bearing surface of the bearing component is pierced with a rod member which is movable longitudinally with respect to the puller body. Finally, the rod member is further moved into engagement with the tapered shaft to force the puller body and bearing component engaged thereby axially off of the tapered shaft after overcoming the frictional engagement of the bearing component and the tapered shaft. After the now-pierced bearing component has been thus removed from the tapered shaft, the rod member is withdrawn therefrom and the pierced bearing component is discarded. A replacement bearing component can then be mounted on the tapered shaft by impaction to achieve a frictional engagement therebetween.

BRIEF DESCRIPTION OF THE DRAWINGS

FIG. 3 is a view similar to that of FIG. 2, with the bearing head puller in piercing engagement with the bearing head.

FIG. 4 is a view similar to that of FIG. 2, with the bearing head puller in engagement with the stem.

DETAILED DESCRIPTION OF THE PREFERRED EMBODIMENTS

Figure 1:
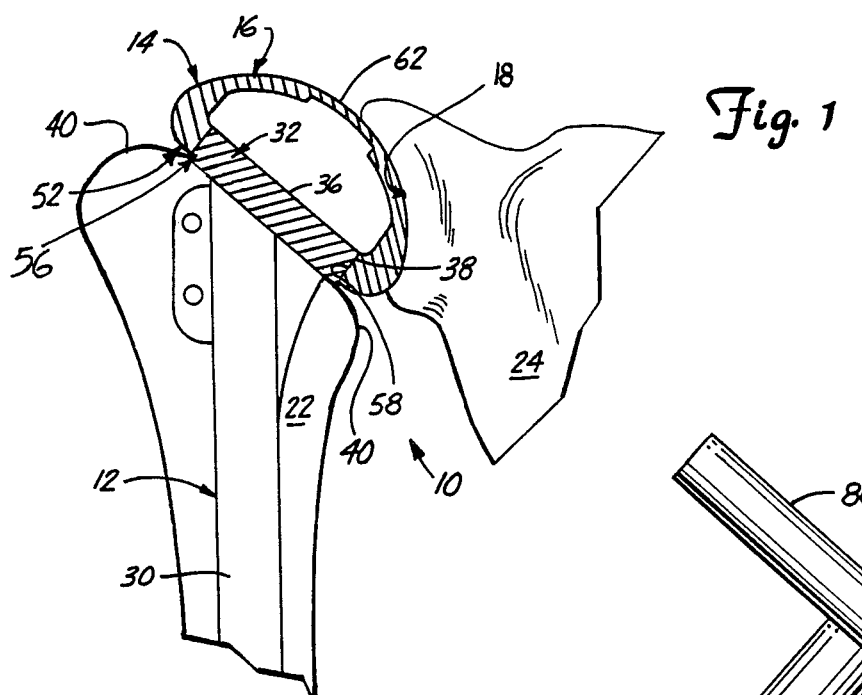
FIG. 1 is an anterior view of the modular prosthetic joint assembly of the present invention, with some parts broken away and shown in section.

In FIG. 1, a prosthetic shoulder joint 10 is shown schematically. While this description is directed primarily to prosthetic shoulder joints, it is contemplated that the prosthetic joint assembly of the present invention is suitable for application to other body joints as well.

The prosthetic shoulder joint 10 includes an elongated stem component 12 and a ball or bearing component 14 which is offset and angled with respect to the central axis of the stem component 12. The bearing component 14 is generally spherical on an outer bearing surface 16 thereof, and that surface articulates with the glenoid fossa 18 of the normal scapula 24, or articulates with a prosthetic glenoid component which resurfaces the glenoid fossa 18 and is secured in the scapula 24. The stem component 12 is mounted within the humerus 22, so that just the bearing component 14 mounted thereon extends upwardly and outwardly from the humerus 22, in operable alignment with the glenoid fossa 18 when the prosthetic joint assembly 10 is assembled as seen in FIG. 1.

The stem component 12 has n elongated body section 30 which is entirely embedded within the humerus 22. A tapered shaft 32 is affixed to or integral with the body section 30 of the stem component 12 at one end thereof. The tapered shaft 32 forms a Morse taper frustum defined about a central longitudinal axis thereof, and as such, the tapered shaft 32 has an end surface 36 at its outermost end and the side walls thereof are defined as angular surfaces 38, with the tapered shaft having a greater diameter adjacent the stem component 12 than at its end surface 36. Preferably, the tapered shaft 32 has a relatively low profile relative to an adjacent outer surface 40 of the humerus 22.

The bearing component 14 defines a bearing head for the prosthetic joint assembly of the present invention, and has a mounting side 52 opposite its outer bearing surface 16. The bearing component 14 has a bore or opening 56 on its mounting side 52. The bore 56 is a female Morse taper with its side walls being defined by angular surfaces 58 which mate with the angular surfaces 38 of the tapered shaft 32. When the bearing component 14 is inserted (and impacted) onto the tapered shaft 32, the angular surfaces thereof mate in a very firm friction fit, and no additional fasteners are required between the bearing component 14 and stem component 12.

The bearing component 14 is generally hollow, like a bell, and opens out through its bore 56 when not mounted on the stem component 12. When the bearing component 14 and stem component 12 are assembled as seen in FIG. 1, however, a central portion 62 of the outer bearing surface 16 extends over the outermost end of the tapered shaft 32, with the central portion 62 formed to be relatively thin in cross section. On its mounting side 52, the bearing component 14 has an annular shoulder portion 64 which extends around the bore 56. The shoulder portion 64 is closely spaced from the outer surface 40 of the humerus 22 when the bearing component 14 is mounted on the tapered shaft 32. While there is a slight gap between the shoulder portion 64 and the outer surface 40, all exposed surfaces of the prosthetic shoulder joint 10 are broadly rounded and smooth in order to resemble a healthy, natural humeral bearing as closely as possible and to minimize any interference with the shoulder's tendons and muscles.

Although hollow (and thus lightweight relative to a solid bearing component), the bearing component 14 is formed from a material of sufficient strength to maintain its rigid structure during use while mated with the glenoid 18. A prosthetic joint assembly of bearing component 14 and stem component 12 (in the form seen in FIG. 1) bears no outward indication that it differs from prior art stem and ball components, whether integral or modular. Functionally, the stem and ball assembly of FIG. 1 (with respect to the socket component 18) is also identical to prior prosthetic joint devices.

For disassembly of the bearing component 14 and stem component 12, however, the differences between the prosthetic joint components of the present invention and the prior art become quite distinct. In the present invention, a bearing head puller 70 is used to disengage the bearing component 14 from the tapered shaft 32 by overcoming the frictional engagement therebetween. The bearing head puller 70 is seen, in various stages of operation, in FIGS. 2-4.

Figure 2:
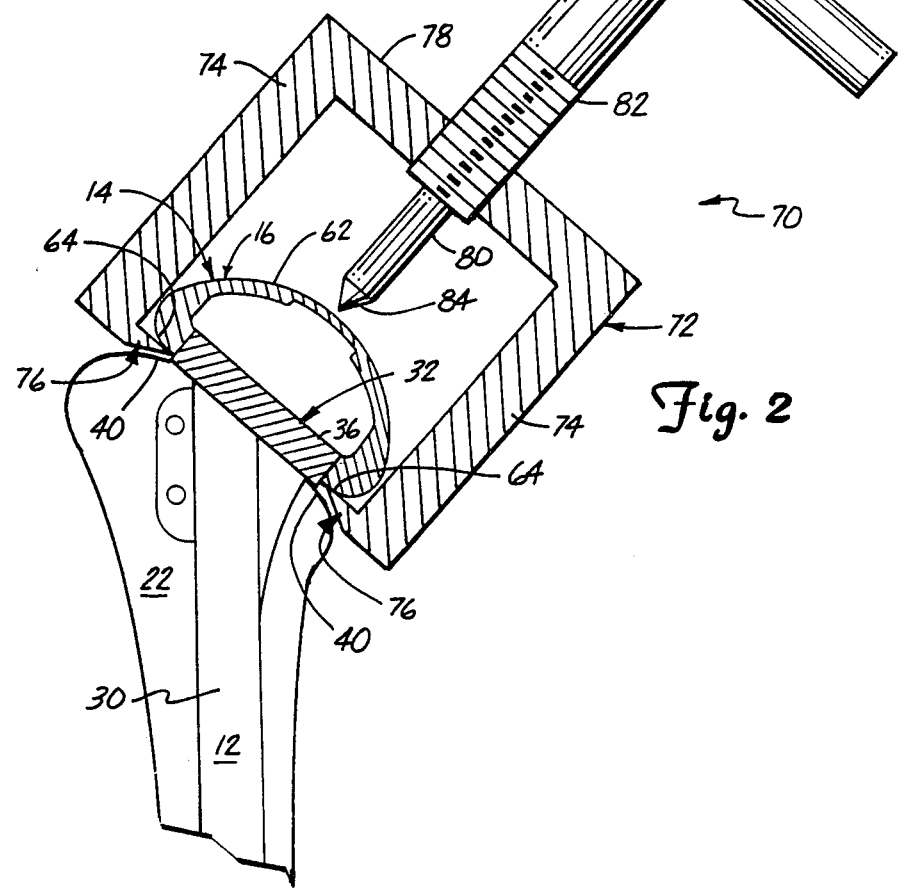
FIG. 2 is a view similar to FIG. 1, also showing the bearing head puller of the present invention aligned about a bearing head.

The head puller 70 includes a puller body 72 which has one or more leg portions 74 adapted to engage the shoulder portion 64 of the bearing component 14. Each leg portion 74 has an inwardly projecting foot 76 which is tapered to fit between the shoulder portion 64 of bearing component 14 and the closely spaced and converging outer surface 40 of humerus 22. The feet 76 engage the shoulder portion 64 of the bearing component 14 along a plane generally normal to the longitudinal axis of the tapered shaft 32. The leg portions 74 are spaced apart sufficient to permit the puller body 72 to be mounted about the bearing component 14, as seen in FIG. 2. Similarly, at some point the feet 76 are spaced apart a distance greater than the largest diameter of the tapered shaft 32 to allow sufficient room for alignment of the bearing head puller 70 about the bearing component 14. The puller body 72 has a central body section 78, which connects the leg portions 74 together and extends over the central portion 62 of the bearing outer surface 60 of the bearing component 14 when the puller body 72 is mounted about the bearing component 14 as seen in FIG. 2.

A pointed rod 80 is mounted to the central body section 78 of the puller body 70 to move axially toward and away from the bearing component 14 along the longitudinal axis of the tapered shaft 32. The pointed rod 80 is mounted on a threaded rod 82, which is threadably mated with central body section 78. The threads are aligned such that turning of the threaded rod 82 in a first rotational direction with respect to the central body section 78 causes the pointed rod 80 to move toward the bearing component 14, as indicated by arrow 83 in FIG. 3. As seen in a comparison of FIGS. 2 and 3, a point 84 of the pointed rod 80 is thus moved into engagement with the central portion 62 of the bearing outer surface 16 of the bearing component 14. Continued turning of the threaded rod 82 forces the point 84 and pointed rod 80 into and through the central portion 62, allowing the point 84 and pointed rod 80 to pass into the hollow internal cavity of the bearing component 14. Further continued rotation of the threaded rod 82 causes the point 84 and pointed rod 80 to move into engagement with the end surface 36 of the tapered shaft 32. Still further continued rotation of the threaded rod 82 forces the point 84 of the pointed rod 80 to bear against the end surface 36 of the tapered shaft 32, and ultimately this bearing force overcomes the frictional engagement force between the angular surfaces 38 and 58 of the tapered shaft 32 and bearing component 14, respectively. At that point, the bearing component 14 separates from the tapered shaft 32 and the feet 76 engaging the shoulder portion 64 of the bearing component 14 urge the bearing component 14 away from the tapered shaft 32 in direction of arrow 85, as seen in FIG. 4. The bearing component 14 and bearing head puller 70 both move away from the tapered shaft 32 in the direction of arrow 85. Turning of the threaded rod is facilitated by a handle 86.

Once disengaged from the tapered shaft 32, the bearing component 14 is completely lifted away from the tapered shaft 32 and can then be replaced by frictional engagement of a new bearing component on the tapered shaft 32. The bearing head puller 70 is reusable by rotating the threaded rod 82 in an opposite rotational direction to withdraw its pointed rod SO from the removed and deformed bearing component 14. The deformed bearing component is then discarded and the bearing head puller 70 is ready for reuse in removing another bearing component.

In one embodiment of the invention, a prosthetic humeral bearing component is machined out of ASTM F-75 Co/Cr/Mo alloy to have an outer spherical radius of 1,000 inches on its bearing or upper side. Because the bearing diameters of prosthetic shoulder joints are much larger than those used in prosthetic hip joints, the Morse taper between the bearing component and stem component can also be larger. By so doing, the larger annular shoulder left on the lower side of the bearing component (about its bore) provides the equivalent of the collar often found on a femoral stem component and provides a means to transfer and distribute loads to the resected humerus. Preferably, the female tapered bore of the bearing component is approximately 1.250 inch diameter by 0.200 inches in length, machined into the lower mounting side (inferior margin) of the bearing component. The humeral bearing component is machined out within the tapered bore section to a concentric spherical radius of 0.920 inches, thus creating a hollow bearing with a dome wall thickness of 0.080 inches. A central portion of the inner dome wall is machined to a 0.970 inch spherical radius, resulting in a 0.500 inch diameter section at the apex of the dome wall having a wall thickness of 0.030 inches.

In a preferred embodiment, a puller body has three leg portions, spaced apart 120 degrees, and the pointed rod is formed of hardened steel with a pointed cylindrical tip of 45 degree included angle. In this configuration, advancement of the pointed rod into engagement with a humeral bearing component initially flattens the central portion of the dome wall slightly, followed by clean piercing or puncturing of the dome wall. Once the dome wall has been penetrated, further advancement of the pointed rod brings it to bear against the humeral stem component, applies a distracting force thereto and through the leg portions of the puller body, pulls the bearing component away from the stem component. The torque required to be applied to the pointed rod is relatively small in order to accomplish the piercing and disengagement of the humeral bearing component from the humeral stem component.

CONCLUSION

The present invention provides a modular prosthetic joint assembly which allows for quick and easy removal of a prosthetic bearing component for replacement or repair. The unique design of the bearing component to be replaced and its accompanying puller device allow a bearing component to be withdrawn from its mounting stem without the application of distraction forces directly against the bone structure of the patient, and without further removal of bone to achieve a bearing surface against which the puller device can react. The bearing component is disfigured during the removal process and is not reusable, but rater designed to be discarded and replaced.

Although the present invention has been described with reference to preferred embodiments, workers skilled in the art will recognize that changes may be made in form and detail without departing from the spirit and scope of the invention.

What is claimed is:

1. In a modular prosthetic joint of the type wherein a bearing head has a bore therein which frictionally mates with a tapered shaft of a stem portion of the joint, the improvement which comprises:
    the bearing head having a generally thin wall defining its continuous and unbroken bearing outer surface, and having a wall portion extending directly over the tapered shaft which is thinner than the remainder of the bearing wall, wherein the wall is thin to permit piercing thereof for the purpose of removing the bearing head from the tapered shaft.

2. The prosthetic joint of claim 1 wherein an inner surface of the thinner wall portion of the bearing head is spaced from an outer end of the tapered shaft when the bearing head is mounted on the tapered shaft.

3. The prosthetic joint of claim 1 wherein the thinner wall portion of the bearing head defines a central area of the bearing outer surface.

4. A kit comprising the prosthetic joint of claim 1, and further comprising:
    puller means for pulling the bearing head away from the tapered shaft by piercing the thin wall thereof.

5. The kit of claim 4 wherein the outer surface of the bearing head defines an annular shoulder portion adjacent and about the bore therein, and the puller means engages the annular shoulder portion of the bearing head and has means associated therewith for engaging and then piercing through the thinner wall portion of the bearing head to engage the tapered shaft and urge the bearing head away from the tapered shaft.

6. In a kit for use in the replacement of a bearing head of a modular prosthetic joint of the type wherein the bearing head has a bore therein and an annular shoulder adjacent to and about the bore, and wherein the bore frictionally mates with a tapered shaft of a stem portion of the joint, with the tapered shaft having a longitudinal axis and an outer end, the improvement which comprises:
    forming a portion of the bearing head which extends over the tapered shaft of relatively thin material;
    a puller body having a plurality of leg portions adapted to engage the annular shoulder portion of the bearing head along a plane generally normal to the longitudinal axis of the tapered shaft; and
    means associated with the puller body for piercing through that portion of the bearing head of relatively thin material to engage the tapered shaft and urge the bearing head away from the tapered shaft, the piercing means being longitudinally movably mounted with respect to the puller body and aligned to move into engagement with that portion of the bearing head of relatively thin material, through such material and into engagement with the outer end of the tapered shaft.

7. The kit of claim 6 wherein the piercing means includes a rod which is threadably mounted with respect to the puller body and which has a pointed end thereof aligned to axially engage the bearing head and outer end of the tapered shaft.

8. A method of removing a bearing head from frictional engagement with the tapered shaft of a joint prosthesis stem, the method comprising the steps of:
    aligning a puller body about the bearing head so that a lower portion of the puller body engages a lower shoulder surface of the bearing head in a plane generally normal to a longitudinal axis defined by the taped shaft;
    piercing an upper being surface of the bearing head with a rod member movable longitudinally with respect to the puller body; and
    urging the rod member into engagement with the tapered shaft to force the puller body and bearing head engaged thereby axially off of the tapered shaft after overcoming the frictional engagement of the bearing head and tapered shaft.

9. The method of claim 8, and further comprising the steps of:
    withdrawing the rod member from its pierced relation with respect to the bearing head; and
    discarding the pierced bearing head.

10. A method of exchanging a bearing head mountable in frictional engagement with the tapered shaft of a joint prosthesis stem, the method comprising the steps of:

aligning a puller body about a first bearing head mounted on the tapered shaft so that a lower portion of the puller body engages a lower shoulder surface of the first bearing head in a plane generally normal to a longitudinal axis defined by the tapered shaft;

piercing an upper bearing surface of the first bearing head with a rod member movable longitudinally with respect to the puller body;

urging the rod member into engagement with the tapered shaft to force the puller body and first bearing head engaged thereby axially off of the tapered shaft after overcoming the frictional engagement of the first bearing head and tapered shaft; and mounting a second bearing head on the tapered shaft by impaction to achieve frictional engagement therebetween.

11. A kit including a prosthetic joint and means for separation of components thereof, the kit comprising:

(a) a stem for affixing substantially within a bone, the stem having a tapered shaft at one end thereof with the tapered shaft being the only portion of the stem extending from the bone and the tapered shaft having an end surface at its outermost end;

(b) a bearing head having a bearing side and a mounting side with a bore in the mounting side adapted for frictional engagement with the tapered shaft, the bearing head having a shoulder portion on its mounting side which extends about the bore and which is closely spaced from the bone, and the bearing head defining a generally spherical bearing outer surface on its bearing side, with a central portion on the bearing outer surface extending over the outermost end of the tapered shaft; and (c) a bearing head puller which includes:

(1) a puller body having a leg portion adapted to engage the shoulder portion of the bearing head between the shoulder portion and adjacent bone and having a central body section aligned to extend over the central portion of the bearing outer surface, (2) a rod member mounted with respect to the central body section of the puller body for movement toward the bearing head, the rod member aligned to move into engagement with the central portion of the bearing outer surface of the bearing head, pierce through that central portion and move into engagement with the end surface of the tapered shaft, and (3) means for urging the rod member toward and through the central portion of the bearing outer surface of the bearing head and against the end surface of the tapered shaft.

* * * * *